(12) United States Patent
Nicholson

(10) Patent No.: US 6,204,034 B1
(45) Date of Patent: Mar. 20, 2001

(54) LEUKOTRIENE $C_4$ SYNTHASE

(75) Inventor: Donald W. Nicholson, Montreal (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 08/196,748

(22) Filed: Feb. 15, 1994

Related U.S. Application Data

(63) Continuation of application No. 07/898,972, filed on Jun. 15, 1992, now abandoned.

(51) Int. Cl.$^7$ .................................................. C12N 9/00
(52) U.S. Cl. ............................................... 435/183
(58) Field of Search .............................................. 435/183

(56) References Cited

PUBLICATIONS

Soberman and Austen, Advances in Prostaglandin, Thromboxane. and Leukothriene Research vol. 19, 21–25 (1989).
Penrose et al (1992) Proc Natl. Acad. Sci., 89, pp. 11603–11606.*
Nicholson et al (1992) Eur. J. Biochem, 209, pp. 725–734.*
Nicholson et al (1992) Journal of Biological Chemistry, 267, pp. 17849–17857.*
Söderström et al. (1992) Archives of Biochemistry and Biophysics 294, pp. 70–74.*
Yoshimoto et al (1988) J. Clin Invest 81, pp. 866–871.*
Yoshimoto et al (1985) Proc. Natl. Acad. Sci 82, pp. 8399–8403.*
Soderstrom et al (1990) Methods of Enzymology 187, pp. 306–312.*

* cited by examiner

Primary Examiner—Jean C. Witz
Assistant Examiner—Michael V. Meller
(74) Attorney, Agent, or Firm—Mollie M. Yang; David L. Rose

(57) ABSTRACT

Leukotriene $C_4$ synthase polypeptide identified by photoaffinity labelling, and purification of leukotriene $C_4$ synthase to homogeneity is described.

3 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (xi) SEQUENCE DESCRIPTION: SEQ ID NO:1:

```
Met Lys Asp Glu Val Ala Leu Leu Ala Ala Val Thr Leu Leu Gly Val
1               5                   10                  15

Leu Leu Gln Ala Gly Phe Ser Leu Gln Val Ile Ser Ala Arg Xaa Ala
            20                  25                  30

Phe Arg Val
        35
```

(2) INFORMATION FOR SEQ ID NO:2:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (xi) SEQUENCE DESCRIPTION: SEQ ID NO:2:

```
Met Lys Asp Glu Val Ala Leu Leu Ala Ala Val Thr Leu Leu Gly Val
1               5                   10                  15

Leu Leu Gln Ala Gly Phe Ser Leu Gln Val Ile Ser Ala Arg Ile Ala
            20                  25                  30

Phe Arg Val
        35
```

(2) INFORMATION FOR SEQ ID NO:3:

(i) SEQUENCE CHARACTERISTICS:
      (A) LENGTH: 35 amino acids
      (B) TYPE: amino acid
      (D) TOPOLOGY: linear (ii) MOLECULE TYPE: peptide (xi) SEQUENCE DESCRIPTION: SEQ ID NO:3:

```
Met Lys Asp Glu Val Ala Leu Leu Ala Ala Val Thr Leu Leu Gly Val
1               5                   10                  15

Leu Leu Gln Ala Gly Phe Ser Leu Gln Val Ile Ser Ala Arg Arg Ala
            20                  25                  30

Phe Arg Val
        35
```

LEUKOTRIENE C$_4$ SYNTHASE

This is a continuation of application Ser. No. 07/898,972 filed Jun. 15, 1992, now abandoned.

BACKGROUND OF THE INVENTION

Leukotrienes (LTs) are products of arachidonic acid metabolism derived through the 5-lipoxygenase pathway. The initial step in LT production involves oxygenation of arachidonic acid to produce 5-hydroperoxyeicosatetranoic acid and a subsequent dehydrase step to produce the epoxide intermediate, LTA$_4$, both enzymic steps being catalyzed by 5-lipoxygenase in association with a 5-lipoxygenase activating protein. Two routes of metabolism of LTA$_4$ lead to the production of biologically active products. LTA$_4$ hydrolase catalyses the stereoselective hydrolysis of LTA$_4$ to produce the dihydroxy fatty acid, LTB$_4$. LTB$_4$ interacts with high-affinity receptor sites to induce leukocyte and lymphocyte activation. A second pathway involves conjugation with glutathione to produce the peptidolipid conjugate, LTC$_4$, this reaction being catalyzed by LTC$_4$ synthase. LTC$_4$ in turn is metabolized to LTD$_4$ by γ-glutamyl transpeptidase and then to LTE$_4$ by a dipeptidase. In the human lung LTC$_4$, LTD$_4$, and LTE$_4$ all interact with a high affinity LTD$_4$ receptor.

Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

SUMMARY OF THE INVENTION

LTC$_4$ synthase has now been identified by photoaffinity labelling and purified to homogeneity. The amino-terminal sequence has been determined from the purified polypeptide.

DETAILED DESCRIPTION

The present invention is related to the purified LTC$_4$ synthase, which in its enzymically active form has a molecular mass of 38±2 kDa and appears to be a homodimer of two 18 kDa subunits. The enzyme is useful in the identification of specific LTC$_4$ synthase inhibitors, in the biosynthetic production of LTC$_4$, and as an antigen for the production of polyclonal and monoclonal antibodies, which in turn could be used to neutralize the enzyme and thereby prevent the production of the pro-inflammatory LTC$_4$.

Monospecific antibodies reactive with LTC$_4$ synthase are purified from mammalian antisera containing antibodies reactive against the enzyme or are prepared as monoclonal antibodies reactive with the enzyme using the technique of Kohler and Milstein, Nature 256:495–497 (1975). Monospecific antibody as used herein is defined as a single antibody species or multiple antibody species with homogeneous binding characteristics for LTC$_4$ synthase. Homogeneous binding as used herein refers to the ability of the antibody species to bind to a specific antigen or epitope, such as those associated with LTC$_4$ synthase, as described herein.

Enzyme specific antibodies are raised by immunizing animals such as mice, guinea pigs, rabbits, goats, horses and the like, with rabbits being preferred, with an appropriate concentration of LTC$_4$ synthase either with or without an immune adjuvant. Pre-immune serum is collected prior to the first immunization. Each animal receives between about 0.1 μg and about 1000 μg of the enzyme associated with an acceptable immune adjuvant. Such acceptable adjuvants include, but are not limited to, Freund's complete, Freund's incomplete, alumprecipitate, water-in-oil emulsion containing *Corynebacterium paryum* and tRNA. The initial immunization consists of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the enzyme in Freund's incomplete adjuvant by the same route. Booster injections are given at about three week intervals until maximal titers are obtained. At about 10–14 days after each booster immunization or about biweekly after a single immunization, the animals are bled, the serum collected, aliquoted and stored at about −20° C.

Monoclonal antibodies (mAb) reactive with LTC$_4$ synthase are prepared by immunizing inbred mice, preferably BALB/c, with the enzyme. The mice are immunized by the IP or SC route with about 0.1 μg to about 10 μg, preferably about 1 μg, of LTC$_4$ synthase in about 0.5 mL buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 μg of the enzyme in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11;S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18 and 21 and are screened for antibody production by an immunoassay such as solid phase immunoradioassay (SPIRA) using the LTC$_4$ synthase as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in "Tissue Culture Methods and Applications", Kruse and Paterson, Eds., 276–280, Academic Press, 1973.

Monoclonal antibodies are produced in vivo by injecting pristane primed BALB/c mice, approximately 0.5 mL per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-$LTC_4$ synthase mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques which are well known in the art. Similar assays are used to detect the presence of $LTC_4$ synthase in body fluids or tissue and cell extracts.

It is readily apparent to those skilled in the art that the above described methods for producing monospecific antibodies may be utilized to produce antibodies specific for $LTC_4$ synthase polypeptide fragments or full-length biologically active enzyme.

ENZYMATIC ASSAYS
Measurement of $LTC_4$ Synthase Activity $LTC_4$ synthase activity was measured by the formation of $LTC_4$ in incubation mixtures containing reduced glutathione (Sigma, St. Louis, Mo.) and $LTA_4$ (free acid) as determined by reverse-phase HPLC following termination of reactions.

Hydrolysis of $LTA_4$ Methyl Ester—The methyl ester of leukotriene $A_4$ was hydrolyzed to the free acid essentially as described by Carrier, D. J. et al., Prostaglandins Leukot. Essent. Fatty Acids, 34, 27–30 (1988). The hydrolysis was monitored by determination of $LTA_4$ by reverse-phase HPLC at pH 10 (Wynalda, M. A. et al., Anal. Chem., 54, 1079–1082 (1982)) except that $LTA_4$ and $LTA_4$-methyl ester were eluted by a gradient of 20 to 70% (v/v) acetonitrile in borate buffer instead of isocratically as described in Wynalda et al. $LTA_4$-methyl ester (1.0 mg in hexane) was dried under a stream of nitrogen and then dissolved in 4 mL of 0.25 M NaOH:acetone (2:8 v/v). Following incubation for 60 min. at 25° C., the hydrolysis mixture was portioned into aliquots that were stored at $-80°$ C. (up to 1 month). Following this procedure, the recovery of $LTA_4$ free acid was >95% as confirmed by analysis of the hydrolysis products by reverse-phase HPLC under alkaline conditions (Wynalda et al.). The longevity of the free acid of $LTA_4$ in incubation mixtures under aqueous condition was substantially improved by: i) the inclusion of 0.05% (w/v) bovine serum albumin in the incubation mixtures, and ii) the use of potassium phosphate as the buffering agent. In their presence, the free acid of $LTA_4$ had a half-life of approximately 30 min. in mock incubation mixtures.

Immediately prior to being used for $LTC_4$ synthase activity measurement (up to 1 hr. preceding the assay), an aliquot of the hydrolysis mixture was thawed, dried under a stream of nitrogen, and dissolved in absolute ethanol to yield a stock concentration of 4 mM $LTA_4$ (100-fold the final concentration in $LTC_4$ synthase incubation mixtures).

Preparation of Serine-Borate Complex—Serine-borate complex was used to inhibit γ-glutamyl transpeptidase activity in order to prevent the conversion of newly-formed $LTC_4$ to $LTD_4$ and then to other leukotrienes (Tate, S. S. et al., Proc. Natl. Acad. Sci. (U.S.A.), 75, 4806–4809 (1978)). Separate solutions of 1 M L-serine and 1 M boric acid were prepared in 10 mM Hepes/KOH (pH 7.4). KOH (from a 10 N stock) was added to re-adjust the pH to 7.4 and improve solubility as necessary (heating was also used when required). Equal volumes of the 1 M L-serine and 1 M boric acid solutions (each at pH 7.4) were then combined (producing a 500 mM stock of serine-borate complex; 10-fold the final concentration in $LTC_4$ synthase incubation mixtures) and stored in aliquots at $-20°$ C. Prior to use, thawed aliquots required warming to 37° C. to redissolve the serine-borate complex.

Preparation of Phosphatidylcholine Suspension—L-α-Phosphatidylcholine (50 mg in 0.5 mL hexane; Sigma Type III-E from egg yolk) was supplemented with 0.25 mg butylated hydroxytoluene (added from a 5 mg/mL stock in chloroform:methanol at 2:1 (v/v)) and then dried completely under a stream of nitrogen. The preparation was redissolved in 0.5 mL absolute ethanol and then diluted with 24.5 mL of 0.1 M KPi ($K_2HPO_4+KH_2PO_4$) pH 7.4 containing 0.1% (w/v) taurocholate (Ultrol grade, Calbiochem, Calif.). The suspension was sonified on ice with 20 pulses at 50% duty cycle using a Branson microtip at 50 W. Aliquots (2 mg L-α-phosphatidylcholine/mL; 10-fold the final concentration in $LTC_4$ synthase incubation mixtures) were stored at $-80°$ C.

$LTC_4$ Synthase Incubation Mixtures—Unless otherwise indicated, $LTC_4$ synthase activity was measured in 0.1 M KPi pH 7.4 buffer (150 µL final volume) in the presence of 50 mM serine-borate complex, 0.2 mg L-α-Phosphatidylcholine/mL, 20 mM $MgCl_2$, 10 mM reduced glutathione and 40 µM $LTA_4$ (free acid, prepared immediately before use by diluting the 4 mM ethanolic stock described above to 0.4 mM with 0.1 M KPi (pH 7.4) containing 5 mg bovine serum albumin/mL, then further diluting this 10-fold directly in the incubation mixtures (giving a final concentration of 40 µM)). The mixtures were incubated for 15 min. at 25° C. and reactions were terminated by the addition of an equal volume (150 µl) of cold (4° C.) acetonitrile:methanol: acetic acid (50:50:1, v/v/v). The mixtures were allowed to stand for a minimum of 30 min. at 4° C. (or overnight). Precipitated proteins were removed by centrifugation at 16,000×g for 15 min. The bulk of the resulting supernatant (250 µl) was then transferred to sample vials for reverse-phase HPLC of which 200 µl was injected for analysis.

Analysis of $LTC_4$ Formation by Reverse-Phase HPLC—The reaction products formed in the incubation mixtures described above were resolved by isocratic reverse-phase HPLC on a Waters Associates Novapak $C_{18}$ column (3.9×150 mm, 4µ particle size). The mobile phase was acetonitrile:methanol:water:acetic acid at 54:14:28:1 adjusted to pH 5.6 with 10 NaOH and was pumped at a flow rate of 1.0 mL/min. $LTC_4$ was quantified by on-line measurement of the optical density at 280 nm. The $LTC_4$ peak was identified by its retention time compared to a synthetic standard (normally 10 min.). In initial experiments to establish the human $LTC_4$ synthase assay, the identity of the $LTC_4$ peak was confirmed by i) retention time similarity with that of synthetic LTC$_4$, ii) leukotriene spectrum determination with an on-time diode array detector, (iii) the presence of $^3$H radioactivity when incubation mixtures contained [14,15-$^3$H (N)]leukotriene A$_4$ (42 Ci/mmol New England Nuclear, Mississauga, Ontario) instead of unlabelled LTA$_4$, iv) the presence of $^{35}$S radioactivity when glutathione was replaced by [$^{35}$S]glutathione (145 Ci/mmol, New England Nuclear), and v) radioimmunoassay.

TISSUE PREPARATIONS

Growth and Isolation of Human Myeloid Leukemia Cells

THP-1 Cell Growth—Cells from the human monocytic leukemia cell line THP-1 (American Type Culture Collection TIB 202; Tsuchiya, S. et al., Int. J. Cancer, 26, 171–176 (1980)) were maintained in culture at 37° C. in a humidified atmosphere containing 6% CO$_2$ in sterile RPMI-1640 medium (supplemented with 0.2% (w/v) NaHCO$_3$, $_{0.03}$% (w/v) L-glutamine and 50 µM 2-mercaptoethanol) containing 10% (v/v) fetal bovine serum (Sigma Hybri-Max, not heat-inactivated), 50 U penicillin/mL and 50 µg streptomycin/mL. Cultures were propagated by subculturing when cell density exceeded 1.5×10$^6$ cells/mL into fresh medium at a seed density of 0.2×10$^6$ cells/mL.

Isolation of THP-1 Cells—For smaller cultures (<8 l), cells were harvested by centrifugation at 600×g for 20 min. at 4° C. The resulting cell pellet was washed by resuspending the cells in the original culture volume in cold (4° C.) PBS (phosphate-buffered saline) (pH 7.4) containing 2 mM EDTA (PBS (pH 7.4), 2 mM EDTA) and re-sedimenting them at 1200×g for 15 min. The washed cells were resuspended in PBS (pH 7.4), 2 mM EDTA with light Dounce homogenization ('B' clearance pestle), adjusted to a final density of 1×10$^8$ cells/mL and stored in aliquots at −80° C. after freezing in liquid nitrogen. Alternatively, for larger cultures (≧8 L), cells were harvested after 4–7 days in culture by continuous-flow centrifugation (Dupont KSB-R/SS-34 rotor) at 5000×g (at r$_{av}$) with a gravity fed flow rate of 400 mL/min. The resulting cell pellet was washed by resuspending the cells in cold (4° C.) PBS (pH 7.4) containing 2 mM EDTA (PBS (pH 7.4), 2 mM EDTA) then re-sedimenting them at 5000×g for 15 min. The washed cells were resuspended in PBS (pH 7.4), 2 mM EDTA with light Dounce homogenization ('B' clearance pestle), adjusted to a final density of 1×10$^8$ cells/mL and stored in aliquots at −80° C. after freezing in liquid nitrogen.

Separation of Cells From Whole Blood

Venous blood was collected from healthy human volunteers and cells were separated by discontinuous gradient centrifugation on Histopaque 1077/1119 (Sigma). The gradient steps were formed by layering 12 mL Histopaque 1077 over 12 mL Histopaque 1119. The freshly-isolated, heparin-treated blood was diluted with an equal volume of PBS (pH 7.2) and 24 mL of the mixture was layered over the Histopaque 1077. The tubes were centrifuged at ambient temperature for 30 min at 700×g (swing out rotor). The monocyte/platelet fraction (at the upper surface of the Histopaque 1077 phase) and the granulocyte fraction (at the Histopaque 1077/1119 interface) were retrieved with pasteur pipets and transferred to new tubes where they were washed by diluting the cells with 5 volumes of PBS (pH 7.2) followed by centrifugation for 20 min at 2000×g. The cell pellet was resuspended in PBS (pH 7.2) and the density was adjusted to 1×10$^8$ cells/mL. Aliquots were stored at −80° C. after freezing in liquid nitrogen.

Preparation of Membrane Fractions

Preparation of Membranes from Cultured Human Myeloid Leukemia Cell Lines (THP-1)—Cells (1×10$^8$ cells/mL) were thawed and supplemented with 2 mM phenylmethylsulfonylfluoride (added from a fresh 200 mM stock in ethanol). The cells were dispersed with 10 strokes in a Dounce homogenizer (with a tight fitting "A" pestle) and then transferred into a nitrogen cavitation cell (Kontes 30 mL/cycle for smaller volumes, Parr for larger volumes up to 500 mL). For each cycle the cavitation unit was pressurized with nitrogen for 15 min. at 800 psi on ice. Following rapid decompression, the cell lysate was collected and spun at 1000×g for 15 min. The pellet was discarded (unless otherwise indicated) and the resulting supernatant was collected and spun at 10,000×g for 20 min. Following centrifugation, the supernatant was retained and re-spun at 100,000×g for 30 min. The resulting microsomal pellet (100,000×g pellet) was retained, washed, and dispersed at a density equivalent to 10$^9$ original cells/mL in PBS (pH 7.4), 2 mM EDTA using a Dounce homogenizer (10 strokes, tight "A" pestle). Aliquots were frozen in liquid nitrogen and stored at −80° C.

Preparation of Membranes from Lung

Postmortem human lung samples were obtained from the International Institute for the Advancement of Medicine (Essington, Pa.) and stored at −80° C. Immediately prior to use, they were rapidly thawed in a water bath at 25° C. All subsequent procedures were performed on ice or at 4° C. Trachea, major airways, large blood vessels and connective tissue were dissected away and the remaining lung tissue (predominantly parenchyma) was rinsed in ice-cold SMEP buffer (0.25 M sucrose, 10 mM MOPS (3-[N-morpholino] propanesulfonic acid)/KOH (pH 7.4), 2 mM EDTA and 2 mM phenylmethylsulfonylfluoride (added from a fresh 200 mM stock in ethanol)). The wet weight of the tissue was determined (after blotting away excess SMEP buffer) and then combined with 1 mL SMEP buffer per g (wet weight) of tissue. The preparation was minced with scissors then diluted with an additional 9 mL SMEP buffer/g original tissue. If necessary, further dispersion was aided by 1–3 min. with an Ultraturrex (coarse generator at 9500 rpm). The suspension was then homogenized by 5 strokes in a Potter-Elvehjem tissue grinder (at approximately 300 rpm) followed by 10 strokes in a ground-glass tissue homogenizer. The suspension was then spun at 1000×g for 15 min. and the resulting supernatant was retained and re-spun a second time at 1000×g for 15 min. The supernatant was collected and spun at 10,000×g for 15 min. followed by re-centrifugation of the resulting supernatant for 30 min. at 100,000×g. The 100,000×g pellet was retained and resuspended in SMEP buffer (at a ratio corresponding to 0.25 mL SMEP buffer per g (wet weight) of original tissue) aided by 10 strokes in a Dounce homogenizer ('A' clearance pestle). Aliquots (typically 10–30 mg protein/mL) were frozen in liquid nitrogen and stored at −80° C.

PHOTOAFFINITY IDENTIFICATION OF THE LTC$_4$ SYNTHASE POLYPEPTIDE

Photoaffinity Labelling

Synthesis of Azido$^{125}$I-LTC$_4$—To a solution of $^{125}$I-NHS-ASC (Ji, T. H. et al., Anal. Biochem., 121, 286–289 (1982)) of the structure:

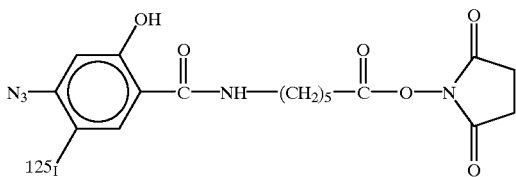

in 200 μl dioxane was added LTC$_4$ (2 mg in 200 μl 1.0 M potassium phosphate buffer pH 7.4). The mixture was stirred at room temperature overnight. Reverse-phase HPLC of the reaction mixture (on a Waters Associates μ-Bondapak C18 column, 3.8×300 mm, using a mobile phase comprised of methanol:H$_2$O:acetic acid:2-mercaptoethanol (75:25:0.1:0.01, v/v) containing 0.5 mM EDTA) afforded the partially purified azido$^{125}$I-LTC$_4$. Repurification using the same solvent conditions (twice) afforded the pure photoaffinity ligand, of the structure:

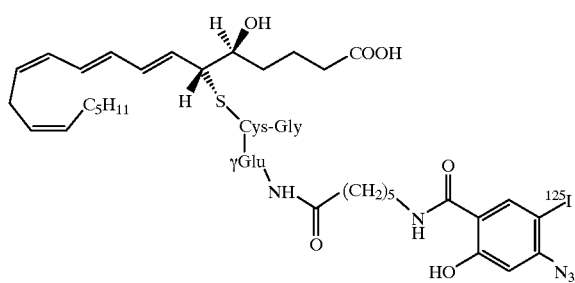

Photoaffinity Labelling of THP-1 Cell Membranes—Incubation mixtures (1.0 mL each) were prepared in a buffer comprised of 20 mM Tris/HCl (pH 7.4), 1 mM EDTA, 1 mM dithiothreitol plus 50 mM serine-borate, containing (unless otherwise indicated) 0.3 mg of THP-1 microsomal membrane protein, 20 pM azido$^{125}$I-LTC$_4$ (introduced in ethanol) plus varying concentrations of competing ligands (either 0.1 to 10 μM LTC$_4$ or 0.1 to 10 mM reduced glutathione). The mixtures were incubated in 1.5 mL microcentrifuge tubes for 30 min. at 25° C. then transferred to 35 mm diameter cluster plate wells for photolysis. The samples in cluster plates were cooled for 5 min. at 4° C. then illuminated from above with a 40W ultraviolet light source (Phillips, $\lambda_{max}$=350 nm) at a distance of 5 cm for 2 min. at 4° C. The samples were then transferred back into 1.5 mL microcentrifuge tubes and the membranes were re-isolated by centrifugation for 15 min. at 200,000×g. The resulting pellets were dissociated in SDS-containing sample buffer, denatured at 95° C. for 5 min. and then the proteins were resolved by SDS-gel electrophoresis. Radioactive bands in the dried gels were visualized by autoradiography and quantified by laser densitometry. Azido$^{125}$I LTC$_4$ specifically radiolabelled a single membrane polypeptide having an estimated molecular mass of 18 kDa.

EXAMPLE 1

PURIFICATION OF LTC$_4$ SYNTHASE TO HOMOGENEITY

All the following procedures were performed either at 4° C. or on ice, unless otherwise indicated.

Detergent Solubilization of LTC$_4$ Synthase—Membrane-bound LTC$_4$ synthase activity was solubilized with 2% (w/v) taurocholate by combining microsomal membrane suspensions (typically 15–20 mg protein/mL) with an equal volume of two-fold concentrated detergent (4% (w/v) taurocholate, unless otherwise indicated) in PBS (pH 7.4), 2 mM EDTA. The mixture was vigorously shaken for 30 min. at 4° C. then spun at 200,000×g for 60 min. at 4° C. The upper ¾ of the resulting supernatant was retained and clarified by passing it first through a 0.45 μM filter (Millex-HA, Millipore) then a 0.22 μM filter (Millex-G, Millipore).

Step 1. Anion-Exchange Chromatography

The taurocholate extract of THP-1 cell microsomal membranes (50 mL, containing 250 to 500 mg protein) was injected onto a HiLoad Q Sepharose HP 26/10 anion exchange column (Pharmacia, 2.6×10 cm) that had been equilibrated in buffer A which was composed of 20 mM Tris/HCl (pH 7.4), 1 mM EDTA, 2 mM reduced glutathione, 1 mM dithiothreitol, 0.1% (w/v) taurocholate, 0.5% (w/v) n-octyl glucoside (Boehringer Mannheim) and 0.5% (w/v) CHAPS (3-[(3-cholamidopropyl)-dimethyl-ammonia]-1-propane sulfonate) (Calbiochem) at a flow rate of 10 mL/min. After washing the column with buffer A, bound proteins were eluted with a linear gradient of NaCl (0 to 1.0 M, 1200 mL gradient volume) in buffer A. LTC$_4$ synthase activity eluted at (ca.) 200 mM NaCl.

Step 2. LTC$_2$ Affinity Chromatography i) Synthesis of LTC$_2$-Biotin: Streptavidin-Agarose Affinity Resins LTC$_2$, a stable analogue of the LTC$_4$ synthase enzyme product LTC$_4$, was synthesized for use as an affinity ligand essentially as described in Spur, B. et al., Tet. Lett., 24, 2135–2136 (1983). Attempts to couple LTC$_2$ to activated affinity supports containing N-hydroxysuccinimide (NHS) esters resulted in low coupling efficiencies (<1%) owing to the poor reactivity of the LTC$_2$ primary amino group. This was circumvented by first biotinylating LTC$_2$ using NHS-esters of biotin (a reaction that went to >90% completion after 6 days with multiple additions of fresh NHS-biotins) and then immobilizing the biotinylated form of LTC$_2$ on streptavidin-agarose (Pierce).

ii) Biotinylation of LTC$_2$

Biotin was linked to the α-amino group of the γ-glutamate component of LTC$_2$ by incubation with N-hydroxysuccinimide esters of biotin having varying spacer arm lengths (13.5 Å, 22.4 Å and 31.3 Å). Reaction mixtures were prepared (200 μl final volume each) containing 1 μmol LTC$_2$ in 10 mM Hepes/KOH pH 7.4. Separate incubation mixtures received either 5 μmol N-hydroxysuccinimidobiotin (NHS-Biotin; 13.5 Å spacer), 5 μmol succinimidyl 6-(biotinamido) hexanoic acid (NHS-X-Biotin; 22.4 Å spacer), or 5 μmol succinimidyl 6-((6-((biotinoyl)amino)hexanoyl)amino hexanoic acid (NHS-XX-Biotin; 31.3 Å spacer), each in 50 μL Me$_2$SO (250 μL final reaction volume). The mixtures were incubated for 6 days at 25° C. during which 3 further additions of the NHS-biotins were made (5 μmol per addition) at 2 hr., 2 days, and 4 days. The reactions were monitored and the final products purified by reverse-phase HPLC on a Waters Associates Novapak C$_{18}$ column (3.9×150 mm, 4μ particle size) with a mobile phase comprised of acetonitrile:methanol:water:acetic acid (54:14:28:1, v/v) plus 1 mM EDTA, adjusted to pH 5.6 with 10 N NaOH and pumped at a flow rate of 1.0 mL/min. $LTC_2$ and its derivatives were monitored by on-line measurement of their optical densities (OD) at 235 nm (retention times were: $LTC_2$=25.7 min., $LTC_2$-biotin=30.4 min., $LTC_2$-X-biotin=33.5 min., $LTC_2$-XX-biotin=35.8 min.).

iii) Immobilization of Biotinylated $LTC_2$ on Streptavidin Agarose

A portion of the HPLC-purified biotinylated $LTC_2$ ($LTC_2$-X-biotin unless otherwise noted) was removed from the stock, dried overnight by vacuum centrifugation, and dissolved in sufficient PBS (pH 7.4), 2 mM EDTA to produce a 25 µM stock solution. (Solubilization was aided by shaking for 5 min. followed by 5 min. of gentle bath sonication and 5 min. shaking. The preparation was then clarified by 5 min. centrifugation at 16,000×g.) Steptavidin-agarose (350 µL bed volume; Pierce) was washed four times with PBS (pH 7.4), 2 mM EDTA and combined with 14 nmol of the $LTC_2$-X-biotin solution in a total volume of 1.5 mL of PBS (pH 7.4), 2 mM EDTA ($LTC_2$-X-biotin was added last into a rapidly mixing slurry in order to ensure uniform distribution of the biotinylated ligand on the streptavidin agarose). After mixing for 15 min. at room temperature, the $LTC_2$-X-biotin was found to be quantitatively bound to the streptavidin agarose. The resulting $LTC_2$-X-biotin:steptavidin agarose affinity resin (having a ligand concentration of 40 µM) was packed into a Pharmacia HR10/2 FPLC column (10 mm diameter×4.5 mm bed height). Nine different columns were constructed having either $LTC_2$-biotin (13.3 Å spacer), $LTC_2$-X-biotin (22.4 Å spacer) or $LTC_2$-XX-biotin (31.3 Å spacer) as the affinity ligand, each at 20, 40, or 80 µM on the support (unless otherwise indicated, affinity chromatography was performed using the 40 µM $LTC_2$-X-biotin:streptavidin-agarose column).

iv) Chromatography

An $LTC_2$ affinity column ($LTC_2$-X-biotin:streptavidin-agarose, 40 µM ligand concentration, 10×4.5 mm) was pre-equilibrated at 1.0 mL/min in running buffer B, which was composed of 20 mM Tris/HCl (pH 7.4), 1 mM EDTA, 1 mM dithiothreitol, 0.1% (w/v) taurocholate, 0.5% (w/v) n-octyl glucoside, 0.5% (w/v) CHAPS (similar to running buffer A except without reduced glutathione). The active fractions from the anion-exchange step were pooled (typically 20 mL in total) and diluted 5-fold into running buffer C to reduce NaCl and glutathione concentrations, both of which inhibited $LTC_4$ synthase binding to the affinity resin. The preparation was then injected onto the $LTC_2$ affinity column at a flow rate of 0.2 mL/min. Following sample application, the flow rate was returned to 1.0 mL/min. and the column was washed with 10 mL running buffer B. $LTC_4$ synthase was eluted with a linear NaCl/reduced glutathione co-gradient (from 0 to 1.0 M NaCl and 0 to 4 mM reduced glutathione; 15 mL gradient volume). $LTC_4$ synthase activity eluted at (ca.) 0.3 M NaCl, 1.2 mM glutathione.

Step 3. Gel Permeation Chromatography

The active fractions from two $LTC_2$ affinity column runs were combined (typically 6 mL in total) then concentrated on a YM-10 ultrafiltration membrane (Amicon) to 0.2 mL and subsequently injected onto a Superdex 75 HR 10/30 column (Pharmacia, 1×30 cm) that had been equilibrated in buffer C, which was comprised of 20 mM Tris/HCl (pH 7.4), 1 mM EDTA, 2 mM reduced glutathione, 1 mM dithiothreitol, 0.1% (w/v) taurocholate, 0.5% (w/v) n-octyl glucoside (Boehringer Mannheim), 0.5% (w/v) CHAPS and 0.25 M NaCl (similar to buffer A except also containing NaCl). $LTC_4$ synthase activity was eluted isocratically at a flow rate of 0.25 mL/min. The active fractions contained a single polypeptide of 18,000 Da on silver-stained SDS-polyacrylamide denaturing gels. The Superdex 75 column was calibrated by performing an identical chromatographic separation of $LTC_4$ synthase co-injected with a mixture (0.4 mg each) of ribonuclease A (13,700 Da), chymotrypsinogen A (25,000 Da), ovalbumin (43,000 Da), bovine serum albumin (67,000 Da) and aldolase (158,000 Da). $LTC_4$ synthase activity eluted at a volume corresponding to a native molecular mass of 38,000±2000. Enzymatically active $LTC_4$ synthase therefore appears to be a homodimer of two 18 kDa subunits.

EXAMPLE 2

SEQUENCE DETERMINATION

Fractions containing the pure 18 kDa polypeptide (approximately 100 pmol) of Example 1 were pooled together and incubated at room temperature for 48 hr. with end-over-end mixing in a tube which also contained a 3×5 mm sliver of PVDF (polyvinylidenedi-fluoride). The sliver was washed several times with water then mounted directly into a sequencer for automated Edman degradation. The amino-terminal sequence of human $LTC_4$ synthase was determined to be that of SEQ ID NO:1 (the single letter amino-acid code above the 3-letter code):

```
M   K   D   E   V   A   L   L   A   A   V   T
Met-Lys-Asp-Glu-Val-Ala-Leu-Leu-Ala-Ala-Val-Thr-
                                L   L   G
                                Leu-Leu-Gly- 15

V   L   L   Q   A   G   F   S   L   Q   V   I
Val-Leu-Leu-Gln-Ala-Gly-Phe-Ser-Leu-Gln-Val-Iso-
                                    S   A   R
                                    Ser-Ala-Arg- 30

X     A   F   R   V
[Xaa]-Ala-Phe-Arg-Val-
``` where X is I (Iso) or R (Arg)

EXAMPLE 3

$LTC_4$ SYNTHASE SPECIFIC ACTIVITY

Following the procedures described above, the following data (the average of duplicate determinations) were obtained from human lung and THP-1 cells. Data are in nmol $LTC_4$ formed•$min^{-1}$•$mg^{-1}$

| Membrane Source | Activity |
| --- | --- |
| Human lung | 0.333 |
| THP-1 Cell | 1.36 |

A representative purification series is shown in Table 1. $LTC_4$ synthase was purified beginning with 2×$10^{11}$ THP-1 cells. $LTC_4$ synthase activity was determined in standard incubation mixtures as described above. The relative specific activity was calculated with respect to the $LTC_4$ synthase specific activity in cells which was set a 1.00.

TABLE 1

$LTC_4$ SYNTHASE PURIFICATION

| Fraction | Volume (mL) | Activity (nmol · min$^{-1}$ · mL$^{-1}$) | Spec. Activity (nmol · min$^{-1}$ · mg$^{-1}$) | Rel. Spec. Activity |
|---|---|---|---|---|
| Harvested Cells | 2000 | 4.364 | 0.151 | 1.00 |
| 100,000x g membranes | 150 | 16.12 | 0.403 | 2.67 |
| Taurocholate extract | 270 | 8.258 | 0.628 | 4.16 |
| HiLoad Q Anion Exchange | 100 | 9.825 | 2.06 | 137 |
| $LTC_2$ Affinity | 30 | 2.492 | 1084 | 7178 |
| Superdex 75 Gel Filtration | 11 | 1.378 | 4135 | 27,384 |

SUMMARY OF PROPERTIES OF HUMAN $LTC_4$ SYNTHASE

| | |
|---|---|
| Optimal Temp.: | 25° C. |
| Optimal pH: | pH 7.4 |
| Linear Range: | up to 200 pmol $LTC_4$ per min. per mL of incubation mix |
| Stability: | requires presence of 2–4 mM reduced glutathione, but less than 5 mM reduced glutathione |
| Prefer'd Substrate: | $LTA_4$ free acid >> $LTA_4$ methyl ester |
| Kinetics: | Human Monocytes: |
| | Km for GSH* = 1.2 mM |
| | Km for $LTA_4$ = 5.6 μM |
| | THP-1 Cells: |
| | Km for GSH = 1.67 mM |
| | Km for $LTA_4$ = 9.89 μM |
| | $V_{max}$ of pure THP-1 = 4.14 μmol · min$^{-1}$ · mg$^{-1}$ |

*Reduced glutathione

What is claimed is:

1. A LTC$_4$ synthase, in substantially free form, having a molecular weight of 18 kDa as determined on silver stained SDS-polyacrylamide denaturing gel and having the partial amino-terminal sequence of SEQ ID NO:1:

```
M   K   D   E   V   A   L   L   A   V   T
Met-Lys-Asp-Glu-Val-Ala-Leu-Leu-Ala-Ala-Val-Thr-
                                    L   L   G
                                    Leu-Leu-Gly- 15

V   L   L   Q   A   G   F   S   L   Q   V   I
Val-Leu-Leu-Gln-Ala-Gly-Phe-Ser-Leu-Gln-Val-Iso-
                                    S   A   R
                                    Ser-Ala-Arg- 30

X   A   F   R   V
        [Xaa]-Ala-Phe-Arg-Val-
``` wherein X is I (Iso) or R (Arg).

2. LTC$_4$ synthase of claim 1 wherein X is I (SEQ ID NO:2).

3. LTC$_4$ synthase of claim 1 wherein X is R (SEQ ID NO:3).

* * * * *